(12) United States Patent
Mermod et al.

(10) Patent No.: US 6,340,741 B1
(45) Date of Patent: *Jan. 22, 2002

(54) POTENT GENETIC SWITCH ALLOWING REGULATED GENE EXPRESSION IN EUKARYOTIC CELLS

(75) Inventors: Nicolas Mermod, Buchillon; Markus O. Imhof, Ecublens; Philippe Chatellard, Lausanne, all of (CH)

(73) Assignee: University of Lausanne, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/370,683

(22) Filed: Aug. 9, 1999

Related U.S. Application Data

(63) Continuation of application No. 09/128,312, filed on Aug. 3, 1998, now Pat. No. 5,989,910.

(51) Int. Cl.$^7$ ............................................... C07K 14/00
(52) U.S. Cl. ......................................... 530/350; 514/152
(58) Field of Search ..................... 435/320.1, 440–465; 536/23.1, 23.4, 24.1; 530/350; 514/152

(56) References Cited

U.S. PATENT DOCUMENTS

| | | | |
|---|---|---|---|
| 5,589,362 A | | 12/1996 | Bujard |
| 5,814,618 A | * | 9/1998 | Bujard et al. ................. 514/44 |
| 5,989,910 A | * | 11/1999 | Mermod et al. ............ 435/325 |

OTHER PUBLICATIONS

Aebischer et al., Nature Medicine 2, 696–699 (1996).
Baniahmad et al., Embo J., 11, 1015–1023 (1992).
Baniahmad et al., Mol. Cell Biol., 15, 76–86 (1995).
Baniahmad et al., Mol. Cell Biol., 17, 4259–4271 (1997).
Deuschle et al., Mol. Cell Biol.. 15, 1907–1914 (1995).
Fisher et al., Mol. Cell Biol., 16, 2670–2677 (1996).
Friedman et al., Genes Dev., 10, 2067–2078 (1996).
Furth et al., Proc. Natl. Acad. Sci., USA, 91, 9302–9306 (1994).
Gossen et al., Proc. Natl. Acad. Sci., 89, 5547–5551 (1992).
Gossen et al., Current Opinion in Biotechnology, 5, 516–520 (1994).
Gossen et al., Science, 268, 1766–1769 (1995).
Grbavec et al., Biochem. Biophys. Res. Com., 223, 701–705 (1996).
Hassig et al., Cell, 89, 341–347 (1997).
Kistner et al., Proc. Natl. Acad. Sci., 93, 10933–10938 (1996).
Magari et al., J. Clin. Invest., 100, 2865–2872 (1997).
Moosmann et al., Nucl. Acids Res., 24, 4859–4867 (1996).
Nagy et al., Cell, 89, 373–380 (1997).
No et al., Proc Natl. Acad. Sci., 93, 3346–3351 (1996).
Palaparti et al., J. Biol. Chem.,272, 26604–26610 (1997).
Resnitzky et al., Mol. Cell. Biol., 14, 1669–1679 (1994).
Rivera et al., Nat. Med., 2, 1028 (1996).
Roelant et al., Bio. Techniques, 20, 914–917 (1996).
Sadowski et al., Nucl. Acids Res., 17, 7539 (1989).
Sadowski et al., Nature, 335, 563–564 (1988).
Smale et al., Cell, 57, 103–113 (1989).
Spencer et al., Science, 262, 1019–1024 (1993).
Thompson et al., Gene, 103, 171–177 (1991).
Wang et al., Proc. Natl. Acad. Sci., 91, 8180–8184 (1994).
Wang et al., Nature Biotechnology, 15, 239–243 (1997).
Wang et al., Gene Therapy, 4, 432–441 (1997).
Witzgall et al., Proc. Natl. Acad. Sci., USA, 91, 4514–4518 (1994).
Yin et al, Analytical Biochemistry, 235, 195–201 (1996).
Yuh et al., Science, 279, 1896–1902 (1998).

* cited by examiner

*Primary Examiner*—Remy Yucel
(74) *Attorney, Agent, or Firm*—Ivor R. Elrifi; Mintz, Levin, Cohn, Ferris, Glovsky & Popeo, P.C.

(57) ABSTRACT

The present invention provides a system for controlled transgene transcription using chimeric activator and repressor proteins functioning in a novel regulatory network. The target transgene is actively silenced in non-inducing conditions by a novel class of chimeric proteins consisting of the DNA-binding tetracycline repressor fused to distinct multimerized eukaryotic transcriptional repression domains. In the presence of a tetracycline "inducer", the repressor does not bind to the promoters for both the target gene and for another regulatory gene encoding a transactivator (e.g., GAL4-VP16). Under these inducing conditions, the transactivator activates expression of the target transgene and of its own gene, in an additional autoregulatory positive feedback loop.

2 Claims, 5 Drawing Sheets ical application is a continuation application under 37 CFR §1.53(b) of U.S. Ser. No. 09/128,312, filed on Aug. 3, 1998 now U.S. Pat. No. 5,989,910, incorporated herein by reference.

POTENT GENETIC SWITCH ALLOWING REGULATED GENE EXPRESSION IN EUKARYOTIC CELLS

This application is a continuation application under 37 CFR §1.53(b) of U.S. Ser. No. 09/128,312, filed on Aug. 3, 1998 now U.S. Pat. No. 5,989,910, incorporated herein by reference.

FIELD OF THE INVENTION

The present invention relates to the regulation of gene expression in eukaryotic cells. More specifically, the present invention relates to a system for controlled transgene transcription using both chimeric activator and repressor proteins.

BACKGROUND OF THE INVENTION

Expression of target genes with homo- and heterologous eukaryotic systems is widely used in biological and medical research, as well as biotechnology and somatic gene therapy. Recently, considerable progress has been made in the control of expression of target genes. Regulated gene expression has been achieved by the use of heterologous or artificial (chimerical) transcription factors responding to an exogenously added inducer drug which acts as a bona fide ligand. Typically, these transcription factors recognize cognate regulatory elements in the promoter of the target gene and the ligand regulates the interaction of the factor with the DNA or the interaction of the DNA-bound factor with a transcriptional activation domain.

Ideally, the administration or removal of the ligand results in a switch between the on or off states of activity of the target gene. Several small molecule ligands have been shown to mediate regulated gene expressions, either in tissue culture cells and/or in transgenic animal models. These include the FK1012 and rapamycin immunosupressive drugs [Spencer et al., Science 262: 1019–1024 (1993); Magari et al., J. Clin. Invest. 100: 2865–2872 (1997)], the progesterone antagonist mifepristone (RU486) [Wang, Proc. Natl. Acad. Sci. USA 93: 8180–8184 (1994); Wang et al., Nature Biotech 15: 239–243 (1997)], the tetracycline antibiotic derivatives [Gossen and Bujard, Proc. Natl. Acad. Sci USA 89: 5547–5551 (1992); Gossen et al., Science 268: 1766–1769 (1995); Kistner et al., Proc. Natl. Acad. Sci. 93: 10933–10938 (1996)], and the insect steroid hormone ecdysone [No et al., Proc. Natl. Acad. Sci USA 93: 3346–3351 (1996)].

One of the major drawbacks with most existing expression systems, however, is the lack of control over the expression level of these target genes which leads to a constitutive production of the encoded recombinant proteins. In most applications, it is desirable to limit the production of such proteins to a defined time window, and to a precisely controlled expression level. This is especially true for the wealth of somatic gene therapy projects including the generation of novel viral and non-viral vectors, or the biotechnological production of recombinant proteins which interfere with cell growth during the exponential phase of cell cultivation in bioreactors. Other examples are found in the analysis of finction and role of specific genes in development and homeostasis of an organism. Therefore, it is imperative to design novel expression systems, the activity of which is under tight genetic control. Such systems are required to exhibit a low (or no) level of transgene expression in the "off-state" and high levels of transgene expression in the "on-state."

Thus, a need remains in the art for a versatile, specific, and stringent genetic switch mechanisms to control target gene expression for the expression of cell-toxic proteins in vitro and for tight transgene regulation in transgenic animals and in gene therapy.

SUMMARY OF THE INVENTION

The present invention relates to a new transgene regulatory system that offers a low background activity when the gene is turned off, a wider window of regulation, and a fast response kinetic after addition of the inducer ligand. The genetic switch system relies on a regulatory network of at least one activator and at least one repressor of transcription, both acting to allow for a high induction window of target gene expression in response to the tetracycline, or a derivative thereof such as doxycycline (dox). Active repression of the transgene in the absence of the inducer drug results in an extremely low background expression level, while autoregulatory positive feedback loops ensure high levels of activated gene expression upon ligand administration. The tight regulation mediated by this regulatory system should prove useful for a variety of applications in biotechnology and medicine.

DETAILED DESCRIPTION OF THE INVENTION

Figure 1A:
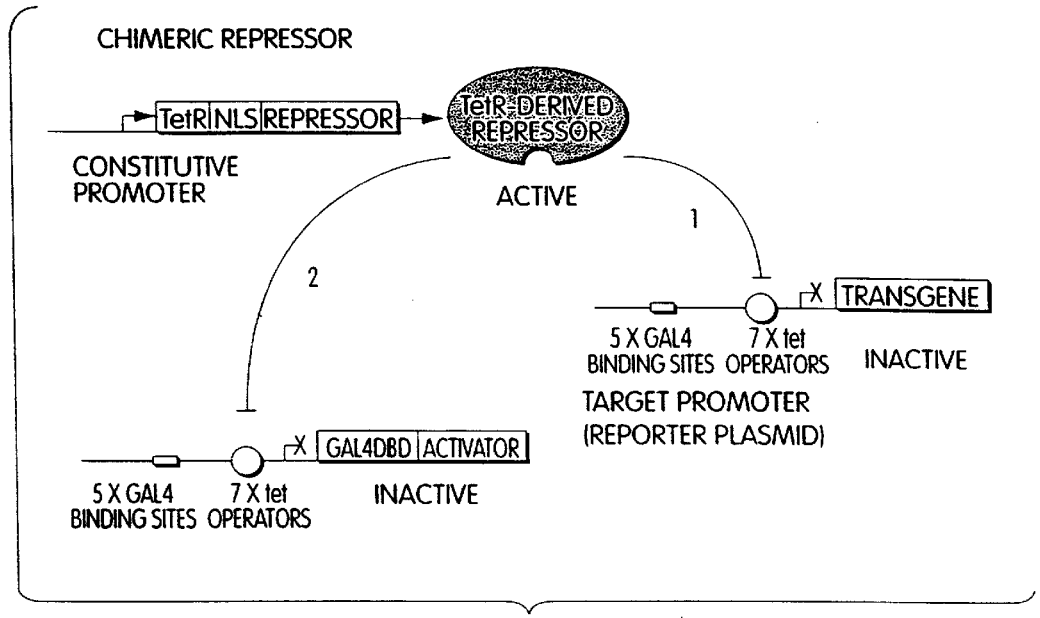
FIGS. 1A and 1B is a schematic representation of the genetic switch mechanism in the "off-state" (Panel A) and in the "on-state" (Panel B), wherein TetR indicates the coding sequences for the tetracycline repressor; NLS represents the coding sequences for the SV40 T-antigen nuclear localization signal; Repressor represents the coding sequences for the eukaryotic transcriptional repressor domains; GAL4 DBD represents the coding sequences for the yeast GAL4 protein DNA binding domain; Activator represents the coding sequences for a transcriptional activation domain, and transgene represents the target transgene. Transcription initiation sites for active and inactive promoters are represented by broken arrows or crossed arrows, respectively. Binding sites for GAL4 and TetR are represented by rectangles and octagonal symbols, respectively.

The present invention provides a regulatory system for controlled transgene transcription. Existing regulatory systems are not versatile, specific, or stringent enough to be of general application. Some of the limitations observed in transgene regulation in the art include, a high background of activity when the gene is turned off, a narrow window of regulation, and a slow response kinetic after addition of the inducer ligand. The regulatory system of the present invention uses chimerical activator and repressor proteins functioning in a novel regulatory network, in order to overcome the limitations of transgene regulation systems in the art. This system exhibits efficient silencing of the target gene in the "off-state," as well as high level activation of the target gene in the "on-state."

The regulatory system of the present invention is an improvement of the well characterized tetracycline repressor protein (TetR) and on a tetracycline derivative inducer. See, e.g., U.S. Pat. No. 5,464,758, incorporated herein by reference. In bacteria, the TetR has been shown to block the expression of bacterial tetracycline resistance genes by binding to specific DNA sequences (TRE) located in the operator. The binding of TetR to tetracycline, or to derivatives such as dox, prevents interaction of TetR with DNA. Gossen et al., Current Opinion in Biotechnology 5: 516–20 (1994). This tetracycline-regulated interaction between TetR and TREs has been used to develop a regulatory system for eukaryotic host cells, where TREs were placed upstream of a minimal eukaryotic promoter and the transactivation domain from the herpes simplex virus VP16 protein was fused to TetR. The presence of dox thus prevents DNA-binding of this chimeric transactivator protein (tTA). Withdrawal of dox has been shown to induce DNA-binding of tTA, which brings upon the activation of the target gene. Gossen and Bujard, Proc. Natl. Acad. Sci USA 89: 5547–5551 (1992). Recently, the replacement of defined amino acids in tTA (rtTA) has lead to the reverse behavior in rtTA activator so its DNA-binding became dox-inducible. Gossen et al., Science 268: 1766–1769 (1995). See, e.g., U.S. Pat. No. 5,589,362, incorporated herein by reference. Although both systems have been shown to reach high levels of target gene activation, these systems suffer from a significant background expression level in the uninduced state.

The novel regulation network of the present invention allows both complete shut-off and efficient activation of the transgene by combining two approaches: (1) an active repression of the target gene by use of TetR fused to multiple transcriptional repression domains; and (2) a tetracycline (e.g., dox) dependent activation of the target gene relying on an autoregulatory feedback loop using conditional expression of a potent eukaryotic transactivator (e.g., a GAL4-VP16 fusion). GAL4 (1-147) binds DNA but does not activate transcription. Sadowski et al., Nature 335: 563–564 (1988). The VP16 fragment is a transactivation domain from the herpes simplex virus VP16 protein.

Figure 1B:
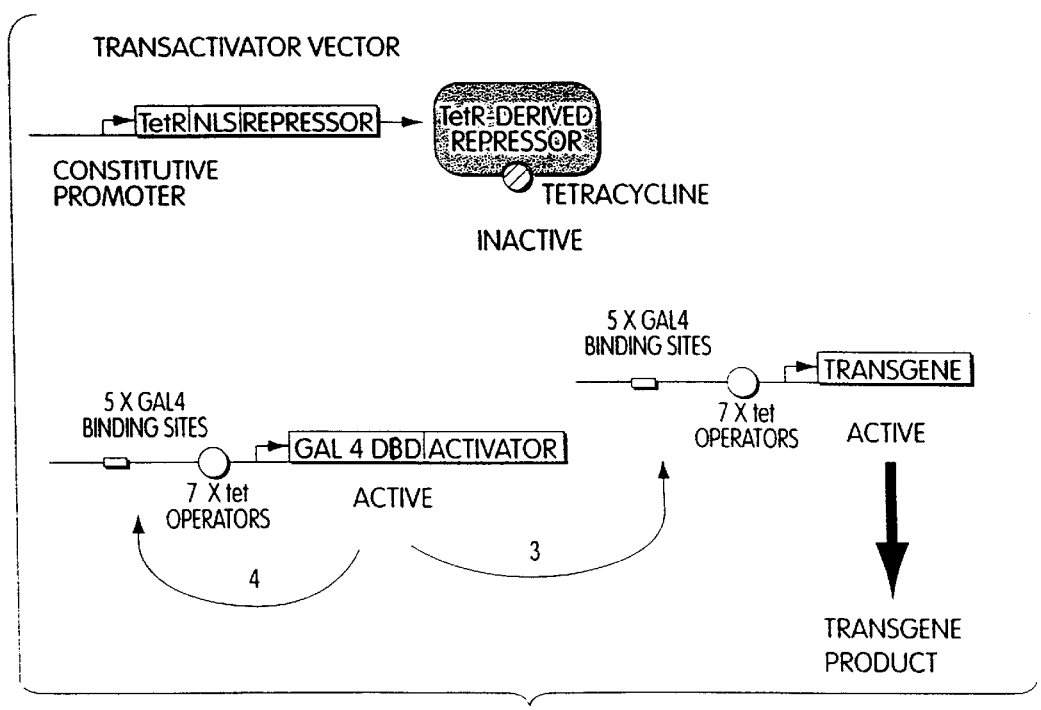

FIG. 1 provides a schematic representation of one embodiment of the genetic switch mechanism in the "off-state" (Panel A) and in the "on-state" (Panel B). In the "off-state," the absence of tetracycline, or a derivative thereof such as dox, allows for efficient binding of the TetR-based chimeric transcriptional repressor, produced from a constitutive promoter, to the target operator sites located in the promoters of the transgene and GAL4-VP16. The binding of the TetR-based repressor to the target operator sites results in efficient silencing of the genes linked to the operators (flat arrows labeled 1 and 2, respectively). In the "on-state," the presence of tetracycline, or a derivative thereof such as dox, inactivates the TetR-based chimeric transcriptional repressors. Low constitutive expression of the activator GAL4-VP16 from its minimal promoter is gradually increased by the positive feedback loop mediated by the GAL4 sites located on the promoter of its own gene (arrow labeled 4). Finally, a level of GAL4-VP16 production is achieved which allows for full transgene expression (arrow labeled 3).

The rationale of this regulatory network consists of controlling transgene expression with two regulatory proteins controlled, either directly or indirectly, by the inducer ligand, at the level of protein activity or at the level of protein synthesis within the cell. Thus, as one of the regulators is placed under the regulation of the other, this creates two layers of regulatory processes that effectively function within a network of cross-regulation to amplify the initial signal triggered by the ligand. Both an activator and a repressor of transcription are needed to achieve tight transgene regulation, so as to actively induce gene expression under inducing conditions or actively repress gene expression under non-inducing conditions.

The specificity of the regulatory process is an important consideration in devising a regulatory pathway, either for gene therapy or for other applications in mammalian cells or organisms. Accordingly, the control of the transgene expression by regulatory pathways endogenous to the host is preferably avoided. In the regulatory system of the present invention, the use of regulatory proteins originating from mammalian cells was limited as much as possible. Regulatory proteins used in the regulatory system of the present invention originate from bacteria, distant eukaryotic cells such as yeast, or from viruses. Only the repression domains are from higher eukaryotes, and in the case of the hormone binding domain of the thyroid receptor, hormonal regulation was specifically disrupted in the TR450W derivative by a deletion within the ligand binding domain. Furthermore, synthetic sequences were used as a backbone for the transgene promoter, thus preventing carry over from unknown regulatory sequences that might result from the use of natural promoters.

In summary, the present invention provides a powerful and stringent, yet versatile regulatory system to gain control over target gene expression. The well-known and advantageous pharmacological properties of the inducer drug, along with the efficient silencing and robust induction of the controlled gene, should prove especially useful for applications which need tight control of the transgene. In addition, the small system size renders it even suitable for protocols that make use of viral vectors with limited capacity.

The tetracycline derivative inducer used in the present invention provides several advantages when considering specificity and safety issues. Although the nature of the inducer ligand may not play an important role in cell culture systems, it is a major concern in applications dealing with whole animals or human beings. Key features of an acceptable ligand for use in mammals are a proven history of safety of use, its specificity for the acceptor protein and target gene regulation (i.e., no cross-reactivity with other regulatory processes), its pharmacological behavior (uptake, kinetics, clearance), its ability to pass the blood brain barrier, and it should be chemically simple and of low production costs, yet it should not be widespread in nature. At present, most of the available systems for ligand-dependent gene regulation are based on drugs which do not fulfill all of the above criteria, because the drugs have known and unwanted pharmaceutical effects or because their specificity and safety has not been evaluated in humans. Therefore, the use in humans of several of these regulatory systems remains questionable as long as the properties of their ligands are not improved and characterized. Tetracycline and dox are acceptable drugs for gene therapy applications, with a long history of safety in human use.

However, the principles of using networks of regulatory proteins, as described in the present invention, are not limited to the TetR and dox molecules, as the use of such networks should be easily adaptable to other inducer compounds and receptor proteins. A skilled artisan will recognize that the regulatory system of the present invention can be based on a different inducer. Several small molecule ligands have been shown to mediate regulated gene expressions, either in tissue culture cells and/or in transgenic animal models. These include the FK1012 and rapamycin immunosupressive drugs [Spencer et al., Science 262: 1019–1024 (1993); Magari et al., Clin. Invest. 100: 2865–2872 (1997)], the progesterone antagonist mifepristone (RU486) [Wang et al., Proc. Natl. Acad. Sci. USA 93: 8180–8184 (1994); Wang et al., Nature Biotech 15: 239–243 (1997)], and the insect steroid hormone ecdysone [No et al., Proc. Natl. Acad. Sci. USA 93: 3346–3351 (1996)].

Moreover, in the regulatory system of the present invention, the transgene is induced by the addition of a ligand. This provides the advantage that induction of the system is not limited by poorly controllable events such as slow disappearance of the ligand, as for the tTA based system. However, a skilled artisan will recognize that a regulatory systems can also be constructed using methods known in the art, wherein the transgene can be induced by the withdrawal of a ligand.

EXAMPLE 1

Molecular Design of the Target Promoter

The commercially available vector pTRE-Luc (Clontech®), which contains seven TREs upstream of the CMV minimal promoter, exhibited high background activity even in the presence of chimeric repressors (data not shown). Accordingly, an artificial promoter was created.

1.1 Plasmid construction

All plasmids of the present invention were generated using techniques well known in the art. After plasmid construction, cloning sites were verified by restriction digestion and sequencing. Fragments derived from PCR amplified DNA were verified by sequencing as well. Plasmids were isolated from cultures of the $E.$ $coli$ strain XL1-blue (Stratagene) by using columns and protocols from Quiagen or Macherey-Nagel. The quality of DNA was checked by gel electrophoresis and quantified by standard measurement of absorbance at a wave length of 260 nm.

The luciferase gene was used as a reporter in the target promoter of the present invention. The use of improved luciferase sequence as a marker gene provides several advantages over other widely used reporters. First, luciferase assays are extremely sensitive and allow faithful measurements of residual activity in the silenced state. Second, luciferase assays are linear over six orders of magnitude which permits accurate parallel comparisons of various systems. Roelant et al., Biotechniques 20: 914–917 (1996). Third, due to its short half-life, luciferase does not accumulate as other reporter enzymes, and thus more closely reflects actual transcriptional activity from the target promoter. Thompson et al., Gene 103: 171–177 (1991). The reporter vector p5xGTTI-Luc+ was cloned using pGL3-Basic (Promega) as a backbone. Expression of luciferase was controlled by the following elements: five GAL4 binding sites, seven TetR response elements, the TATA box from the adenovirus major late promoter, and the initiator of the terminal deoxynucleotidyl transferase gene.

1.2 Cell culture and transfection

Baby hamster kidney 21 (BHK 21) cells were cultivated in DMEM (Gibco-BRL) supplemented with 10% FCS (Gibco-BRL). For transfectiors, cells were seeded in 24 well plates at about 40% confluency and allowed to attach to the surface. After washing with PBS, cells were exposed to the transfection mix for 4 hours. Thereafter, the transfection mix was replaced by medium which contained, where indicated, 100 ng/ml doxycycline hydrochloride (Sigma #D9891). Generally, medium was replaced every 24 hours and cells were harvested 48 hours post-transfection.

BHK cells were co-transfected with 81 ng of the luciferase reporter plasmid (i.e., construct p5xGTTI-Luc+ depicted in FIG. 1) containing luciferase-plus as the transgene, 810 ng of a vector encoding VSV40 early promoter/enhancer-driven TetR sequence fused to an NLS and the eukaryotic repressor KoxW, and 162 ng of the pCMVβGal β-galactosidase internal standardization construct per triplicate. Thus, the only regulatory component of the present target promoter is the dox-relieved repression of the transgene (arrow labeled 1 in FIG. 1).

All transfections were made in triplicate and repeated several times. Transfection mixes were brought to a total DNA amount of 2430 ng per triplicate with pUC18. In a polystyrene tube (Falcon #2057), 77 µl of OptiMEM were combined with 4 µl of Lipofectin® (Gibco-BRL) per triplicate and incubated for 30 min. Subsequently, the DNA and Lipofectin® mixes were combined in a polystyrene tube, and after another 15 min of incubation at room temperature, each mix was supplemented with 1 ml of OptiMEM per triplicate. Each cell culture well was then exposed to 300 μl of the transfection mix.

1.3 Extract preparation and enzymatic measurements

For luciferase and β-galactosidase measurements, cell extracts were prepared as follows. Cells were washed with PBS, incubated with 100 μl lysis buffer (25 mM Tris-phosphate, pH 7.8, 2 mM DTT, 2 mM CDTA (Sigma #D1383), 10% glycerol, 0.5% Triton X-100) for 20 min at room temperature, 50 μl of extract were transferred into a flat bottom 96 well tissue culture plate, thereof 20 μl were transferred into a white 96 well plate for subsequent luciferase measurement in a EG&G Berthold Microplate 96V luminometer. The constant glow type assay for luciferase was performed using the reagents from a kit (Promega #E1501). For each well 100 μl substrate solution was added by injection. After a delay of 2 sec light emission was measured for 2 sec.

Colorimetric determination of β-galactosidase activity was performed by adding 150 μl CPRG buffer (60 mM $Na_2HPO_4$ 7 $H_2O$, 40 mM $NaH_2PO_4$, 10 mM KCl, 1 mM $MgSO_4$, 50 mM β-mercaptoethanol) and 20 μl CPRG solution (Boehringer Mannheim #884308, 4 mg/ml in $H_2O$) to the remaining 30 μl cell extract in the 96 well plate. Assays were performed at 37° C. and simultaneously stopped by addition of 100 μl 1 M sodium carbonate (containing 0.5 μl of Antifoam A per ml). Absorbance was measured at 575 nm in a plate reader (Spectramax 340, Molecular Devices) and samples were normalized to wells in which lysis buffer was assayed.

Relative light units were calculated by normalizing luciferase for β-galactosidase activity. Data points represent the average of the specific triplicate and error bars indicate the standard error.

Figure 2:
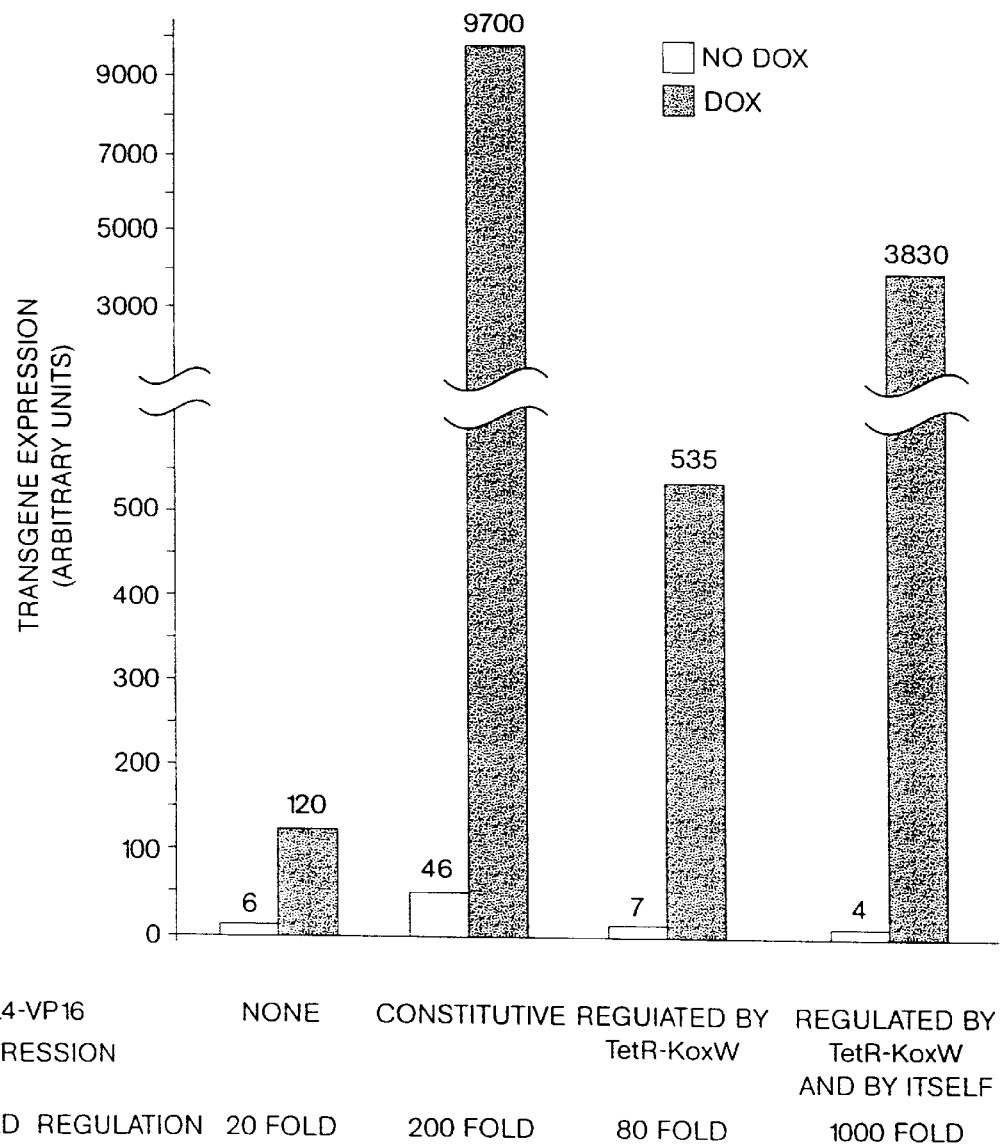
FIG. 2 is a bar graph depicting the transgene expression of BHK cells co-transfected with the luciferase reporter plasmid, internal standardization constructs and the pSV-TetRNLS-KoxW expression vector for the KoxW fusion repressor in the absence of GAL4-VP16 expression vector (none), or with the constitutive expression vector for GAL4-VP16 pBKC-GAL4VP16 (constitutive), the pTTI-GAL4VP16 expression vector containing TetR operator binding sites alone (regulated by TetR-KoxW), or the p5xGTTI-GAL4VP16 expression vector containing both TetR operators and GAL4 binding sites (regulated by TetR-KoxW and by itself). Cells were incubated in presence (solid bars) or absence (open bars) of 100 ng/ml of dox. Transgene expression of luciferase was normalized to that of β-galactosidase and is expressed in relative light units.

As depicted in the leftmost most data set of FIG. 2 (None), in the absence of an active repressor (closed bar), this artificial target promoter exhibited low but clearly measurable basal activity when transiently transfected into host cells.

EXAMPLE 2
Molecular Design of Novel Chimeric Repressors by the Fusion of Heterologous Repression Domains In order to identify efficient transcriptional repressors, a series of artificial chimeric repressors was evaluated in combination with the reporter plasmid. Repressors included the hormone-binding domain of rat thyroid hormone receptor β (TRHBD) [Baniahmad, et al., EMBO J. 11: 1015–1023 (1992)], the KRAB domain of Kox1 [Witzgall et al., Proc. Natl. Acad. Sci. USA 91: 4514–4518 (1994)], and the four amino acids WRPW motif at the carboxyl terminus of Drosophila hairy proteins [Fisher et al., Mol. Cell. Biol. 16: 2670–2677 (1996)]. The selected eukaryotic repression domains, and derivatives thereof, were fused downstream of the sequence encoding TetR and the nuclear localization signal (NLS) from the SV40 large T antigen. The repressive potential of these factors was compared with unfused TetR as a negative control.

2.1 Plasmid construction

As described in Example 1.1, cloning sites were verified by restriction digestion and sequencing after plasmid construction. Fragments derived from PCR amplified DNA were verified by sequencing as well. Plasmids were isolated from cultures of the E. coli strain XL1-blue (Stratagene) by using columns and protocols from Quiagen or Macherey-Nagel. The quality of DNA was checked by gel electrophoresis and quantified by standard measurement of absorbance at a wave length of 260 nm.

The coding region for TetR was PCR-amplified from pTet-Off® (Clontech®) with the primers:

5'-CGGAATTCACCATGTCTAGAT TAGATAAAAG-TAAAG (SEQ ID NO:1) and

5'-CGGGATCCACTTTCACATTTAAGTTGTTTT (SEQ ID NO:2).

The resulting fragment was restricted with EcoRI and BamHI and subcloned into pBSII+KS (Stratagene). A first generation of CMV-based expression vectors was made by transferring the coding region of TetR as a SalI-BamHI fragment into pBKCMV (Stratagene). This vector, which encodes 34 additional amino acids following the coding region of TetR, was used as a parent for further constructs.

2.11 pBKC-TetRStop

A control vector, pBKC-TetRStop, was created by digestion of the above-described plasmid (Example 2.10) with BamHI and XhoI, fill-in reaction with Klenow enzyme, and re-legation leading to a TetR with four additional unrelated amino acids at its carboxyl terminus. Alternatively, the nuclear localization signal (NLS) from the SV40 large T antigen was added by using the annealed oligonucleotides:

5'-GATCTCCAAAAAAGAAGAGAAAGG (SEQ ID NO:3) and

5'-GATCCCTTTCTCTTCTTTTTTGGA (SEQ ID NO:4) and inserting them into the BamHI site of the parent vector. This recreated a unique BamHI site at the 3' end of the TetRNLS coding region which permitted in-frame fusion of repression domains, as described below.

2.12 pBKC-TetRNLS-WRPW

To create pBKC-TetRNLS-WRPW, the oligonucleotides

5'-GATCCTGGAGACCATGGTAGC (SEQ ID NO:5) and

5'-GGCCGCTACCATGGTCTCCAG (SEQ ID NO:6)
were annealed and inserted between the BamHI and NotI sites.

2.13 pBKC-TetRNLS-TRHBD

The primers

5'-CGGGATCCGGCATGGCAACAGACCTGG (SEQ ID NO:9) and

5'-GGCGGCCGCTCAGTCCTCAAAGACTTCCAA (SEQ ID NO:10)

were used to generate a PCR fragment encoding the hormone binding domain (amino acids 168 to 456) of the rat TRβ. This fragment was cloned downstream of the NLS by the use of BamHI and NotI restriction sites, leading to plasmid pBKC-TetRNLS-TRHBD.

2.14 pBKC-TetRNLS-Kox pBKC-TetRNLS-Kox was created by inserting the PCR fragment encoding amino acids 1–89 of human Kox-1, generated with primers:

5'-CGAGATCTTTGACTGTATCGCCGGAATTC (SEQ ID NO:7) and

5'-GGCGGCCGCTAGGATCCAGTCTCTG AATCAG-GATGGGT (SEQ ID NO:8)

after cleavage with BglII and NotI. This destroyed the BamHI site at the end of the NLS by ligating the compatible BglII site. However, a new BamHI site was generated at the carboxyl terminus of the coding region just upstream of the stop codon followed by the NotI site.

2.15 pSVtetR derivatives

TetR constructs were recloned as a HindIII-NotI fragments into a derivative of pSG424 [Sadowski & Ptashne, Nucl. Acids Res. 17: 7539 (1989)] in which a NotI site was previously inserted immediately preceding the XbaI site and stop codons. The resulting plasmids are called pSV-TetR STOP, pSV-TetRNLS-WRPW, pSV-TetRNLS-TRHBD, and pSV-TetRNLS-Kox.

2.2 Cell culture and transfection

The BHK 21 tissue culture cell line was cultivated and transfected essentially as described in Example 1.2. Briefly, cells were seeded in 24 well plates at about 40% confluency and allowed to attach to the surface. After washing with PBS, cells were exposed to the transfection mix for 4 hours. Thereafter, the transfection mix was replaced by medium which contained, where indicated, 100 ng/ml dox hydrochloride (Sigma #D9891). Generally, medium was replaced every 24 hours and cells were harvested 48 hours post-transfection.

BHK cells were co-transfected with 81 ng of construct p5xGTTI-Luc+ containing luciferase-plus as the transgene, 162 ng of the pCMVβGal β-galactosidase internal standardization construct, 16 ng of the pBKC-GAL4VP16 constitutive (cytomegalovirus) promoter-driven GAL4-VP16 expression construct. In addition, BHK cells were co-transfected with 810 ng of a vector encoding SV40 early promoter/enhancer-driven TetR sequence alone or fused to an NLS and one of the following repression domains: Drosophila hairy (WRPW), rat thyroid receptor (TR-HBD), or human Kox1 (Kox) proteins.

Again, all transfections were made in triplicate and repeated several times. Transfection mixes were brought to a total DNA amount of 2430 ng with pUC18. In a polystyrene tube (Falcon #2057), 77 µl of OptiMEM were combined with 4 µl of Lipofectin® (Gibco-BRL) per triplicate and incubated for 30 min. Subsequently, the DNA and Lipofectin® mixes were combined in a polystyrene tube, and after another 15 min of incubation at room temperature, each mix was supplemented with 1 ml of OptiMEM per triplicate. Each cell culture well was then exposed to 300 µl of the transfection mix.

2.3 Extract preparation and enzymatic measurements

Figure 3:
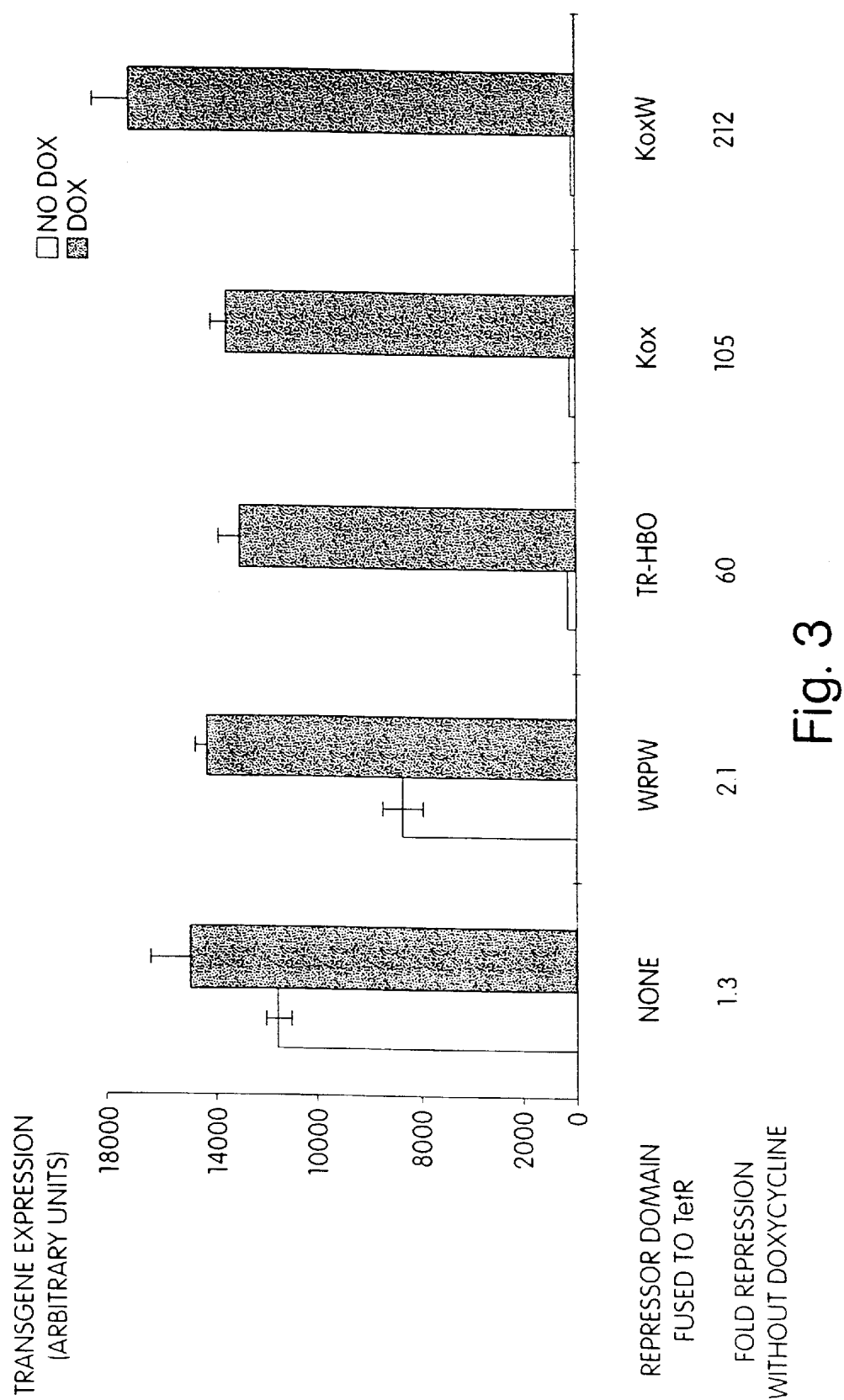
FIG. 3 is a bar graph depicting the transgene expression in presence or absence of natural and chimeric repression domains fused to TetR in the presence (solid bars) or absence (open bars) of 100 ng/ml dox. BHK 21 cells were co-transfected with construct p5xGTTI-Luc+ containing luciferase-plus as the transgene, the pCMVβGal β-galactosidase internal standardization construct, the pBKC-GAL4VP16 constitutive (cytomegalovirus) promoter-driven GAL4-VP16 expression construct, and the vector encoding SV40 early promoter/enhancer-driven TetR sequence without a repressor domain (None), or with the repression domain of the Drosophila hairy (WRPW), rat thyroid receptor (TR-HBD), human Kox1 (Kox) proteins, or those of both Kox1 and hairy (KoxW), as indicated.

Extract preparation and enzymatic measurements were conducted essentially as described in Example 1.3. As shown in FIG. 3, in the absence of dox, diverse repressive strengths on the luciferase reporter activated by constitutive GAL4-VP16 expression were detected. The WRPW motif had only a limited repressive effect, whereas strong repression of the target promoter was observed with TRHBD and Kox. As expected, the addition of the dox ligand abolished the repression.

EXAMPLE 3

Multimerization of Distinct Repression Domains

A prerequisite for the effectiveness of the regulatory networks is active and efficient silencing of the target promoter in non-inducing conditions. Repression domains are thought to function in vivo by recruiting specific corepressor proteins which are part of a macromolecular silencing complex. For instance, TR has been shown to recruit the corepressors Sin3A, human histone deacetylase 1 (HDAC1) as well as N-COR Baniahmad et al., Mol Cell Biol 17: 4259–4271 (1997); Nagy et al., Cell 89: 373–380 (1997); Hassig et al., Cell 89: 341–347 (1997). Kox1 has been shown to recruit KAP-1 and TIF1b [Friedman et al., Genes Dev 10: 2067–2078 (1996); Moosmann et al., Nucl. Acids Res. 24,4859–4867 (1996)], and the WRPW motif recruit TLE1 [Grbavec & Stifani, Biochem Biophys Res Com 23: 701–705 (1996)] which in turn is able to mediate silencing by contacting histone H3. Palaparti et al., J. Biol. Chem. 272: 26605–26610 (1997). However, repression obtained by directly targeting the corepressors to the target promoter was not as efficient as that observed with the parental DNA-binding repressors (data not shown), possibly because the latter might use several pathways and corepressor proteins to inhibit gene expression. Therefore, an alternative approach was taken. Multimerization of distinct transcriptional activation domains has been shown to act synergistically to generate more active transactivator proteins. See, Wang et al., Nature Biotech 15: 239–243 (1997).

Similarly, in the present Example, two distinct repression domains were fused to TetR within the same repressor molecule in order to investigate the possibility that fused transcriptional repressors may also synergize to inhibit transcription.

Moreover, to further assess the properties of the regulatory system of the present invention, the functioning of the two multimeric repression constructs was evaluated in $C_2C_{12}$ cells. $C_2C_{12}$ is another cell line currently employed in ex vivo gene therapy protocols that make use of in vitro transfected cells expressing therapeutic genes.

3.1 Plasmid construction

The coding sequence for the short WRPW sequence was fused at the carboxyl terminus of other repression domains including those of Kox1 and of the thyroid receptor, yielding the KoxW and $TR_{450}W$ constructs, respectively.

3.11 pBKC-TetRNLS-KoxW pBKC-TetRNLS-KoxW was created by inserting the oligonucleotides encoding the WRPW motif (see above) into the BamHI-NotI sites in pBKC-TetRNLS-Kox.

3.12 pSV-TetRNLS-$TR_{450}W$ pSV-TetRNLS-$TR_{450}W$ was created by replacing the BamHI-NotI in pSV-TetRNLS-TRHBD with a PCR fragment obtained with the oligonucleotides:

5'-CGGGATCCGGCATGGCAACAGACCTGG (SEQ ID NO:9) and

5'-GGCGGCCGCTACCAAGGTCTCCATGGGA AGAGAGGCGGGAAGAG (SEQ ID NO:11).

This replaces the last six amino acids of the HBD with a proline and the WRPW motif. These C-terminal six amino acids of the thyroid receptor hormone-binding domain were deleted to render the HBD insensitive to thyroid hormones, a prerequisite for the use of such a construct in humans. Baniahmad et al., Mol. Cell Biol. 15: 76–86 (1995); Baniahmad et al., Mol. Cell Biol. 17: 4259–4271 (1997). To create an expression vector driven by the mouse PGK promoter, the SV40 promoter in pSV-TetRNLS derivatives was removed by digestion with PvuII and BglII. After a fill-in reaction and re-ligation, the promoter and first intron of the mPGK gene were inserted as a HindIII-EcoRI fragment, yielding pPGK-TetRNLS-$TR_{450}W$.

The constitutive CMV-driven expression vector pBKC-GAL4VP16 was created by sequentially inserting the GAL4 DNA-binding domain as a BglIII-RI fragment from pSG424 and the VP16 transactivation domain as an EcoRI-BamHI fragment into pBKCMV (Stratagene) in which a BamHI site was previously inserted upstream of the XbaI site.

3.2 Cell culture and transfection

The BHK 21 and $C_2C_{12}$ tissue culture cell lines were cultivated and transfected essentially as described in Example 1.2. Briefly, cells were seeded in 24 well plates at about 40% confluency and allowed to attach to the surface. After washing with PBS, cells were exposed to the transfection mix for 4 hours. Thereafter, the transfection mix was replaced by medium which contained, where indicated, 100 ng/ml dox hydrochloride (Sigma #D9891). Generally, medium was replaced every 24 hours and cells were harvested 48 hours post-transfection.

BHK cells or $C_2C_{12}$ cells were co-transfected with 162 ng of pVG-GTTI-Luc+ (a fusion of the p5xGTTI-GAL4-VP16 expression vector and p5xGTTI-Luc+ reporter with bi-directional transcriptional regulation), 162 ng of the pCMVβGal, and 810 ng of either pSV-TetRNLS-$TR_{450}W$ or pSV-TetRNLS-KoxW Again, all transfections were made in triplicate and repeated several times. Transfection mixes were brought to a total DNA amount of 2430 ng with pUC18. In a polystyrene tube (Falcon #2057), 77 µl of OptiMEM were combined with 4 µl of Lipofectin® (Gibco-BRL) per triplicate and incubated for 30 min. Subsequently, the DNA and Lipofectin® mixes were combined in a polystyrene tube, and after another 15 min of incubation at room temperature, each mix was supplemented with 1 ml of OptiMEM per triplicate. Each cell culture well was then exposed to 300 µl of the transfection mix.

3.3 Extract preparation and enzymatic measurements

Extract preparation and enzymatic measurements were conducted essentially as described in Example 1.3.

Specific configurations brought upon a significant improvement of the silencing activity. For instance, the simple addition of the WRPW motif at the carboxyl terminus of another repression domains led to a tighter control. Inclusion of WRPW increased the repressive strength of the KoxW (FIGS. 2–4) and $TR_{450}W$ (FIG. 4) constructs, and that of the Wilms tumor supressor protein WT1 (data not shown), as compared to constructs with a single repression domain. These results indicate that specific repression domains can act synergistically with one another to inhibit gene transcription, suggesting that various corepressor complexes might be contacted simultaneously resulting in more complete silencing at the target promoter, which can be used to generate novel and more efficient repressors than those occurring naturally.

Further, the KoxW and $TR_{450}W$ constructs inhibited gene transcription in both BHK and $C_2C_{12}$ cells. As illustrated in FIG. 4A, transient transfection of $C_2C_{12}$ cells yielded high level of regulation, generating up to 700 fold increase in the expression of the transgene in response to dox treatment, as previously observed in BHK cells.

In summary, the use multiple repression domains which are intramolecularly fused to each other and to TetR provide a convenient novel tool for generating powerful artificial repressors.

EXAMPLE 4
Construction of an Autoregulatory Positive Feedback Loop that Mediates Wide Induction Windows for the Transgene As discussed in Examples 2 and 3, although the chimeric repressors of transcription efficiently repress the basal (non-induced) level of transgene expression, they did not fully repress transcription when induced by potent activators. Conversely, even the potent GAL4-VP16 activator is unable to fully activate a promoter associated with a transcriptional repressor. These findings suggest that the mere combination of activators and repressors of transcription is unlikely to suffice for tight gene control.

To alleviate high basal level of expression in absence of doxycycline, the expression of GAL4VP16 was placed under the control of TetR-based chimeric repressors. This allowed low levels of basal expression, but also decreased activated expression in presence of doxycycline. See, for example, the two middle data set of FIG. 2. In order to assess whether the expression of GAL4VP16 may limit activated levels of transgene expression, five GAL4 responsive sites were inserted in the promoter driving GAL4-VP16 expression, with the aim of creating a positive feedback loop in which GAL4-VP16 could promote its own expression.

4.1 Plasmid construction

In order to remove the coding region of luciferase, p5xGTTI-Luc+ was restricted with NcoI and Eco47III, filled by Kenow enzyme, and religated. A HindIII fragment encoding GAL4VP16 was then inserted to create the conditional expression vector p5xGTTI-GAL4VP16. pTTI-GAL4VP16 is identical to p5xGTTI-GAL4VP16, except that the GAL4 sites were not inserted.

4.2 Cell culture and transfection

BHK 21 cells were cultivated and transfected essentially as described in Example 1.2. BHK cells were co-transfected with 81 ng of the luciferase reporter plasmid containing luciferase-plus as the transgene, 162 ng of the pCMVβGal β-galactosidase internal standardization construct, 810 ng of the pSV-TetRNLS-KoxW expression vector for the KoxW fusion repressor, and 16 ng of the pTTI-GAL4VP16 expression vector containing TetR operator binding sites alone (i.e., regulated by TetR-KoxW), or of the p5xGTTI-GAL4VP16 expression vector containing both TetR operators and GAL4 binding sites (i.e., regulated by TetR-KoxW and by itself). Thus, an additional regulation loop is implemented for GAL4-VP16 expression in the expression vector containing both TetR operators and GAL4 binding sites (arrows labeled 1, 2, 3 and 4 of FIG. 1) when compared to the expression vector containing TetR operator binding sites alone (arrows labeled 1, 2 and 3 of FIG. 1).

Again, all transfections were made in triplicate and repeated several times. Transfection mixes were brought to a total DNA amount of 2430 ng with pUC18. In a polystyrene tube (Falcon #2057), 77 µl of OptiMEM were combined with 4 µl of Lipofectin® (Gibco-BRL) per triplicate and incubated for 30 min. Subsequently, the DNA and Lipofectin® mixes were combined in a polystyrene tube, and after another 15 min of incubation at room temperature, each mix was supplemented with 1 ml of OptiMEM per triplicate. Each cell culture well was then exposed to 300 µl of the transfection mix.

4.3 Extract preparation and enzymatic measurements

Extract preparation and enzymatic measurements were conducted essentially as described in Example 1.3.

As depicted in the two right-most data sets in FIG. 2, in the presence of dox (i.e., in the activated state), the transgene expression was significantly greater in the expression vector containing both TetR operators and GAL4 binding sites when compared to the expression vector containing TetR operator binding sites alone. This suggests that low constitutive expression of the activator GAL4-VP16 from its minimal promoter is gradually increased by the positive feedback loop mediated by the GAL4 sites located on the promoter of its own gene (arrow labeled 4 in FIG. 1), thereby permitting a level of GAL4-VP16 to be reached which allows for full transgene expression (arrows labeled 3 in FIG. 1). Using this positive feedback loop, an induction window of over three orders of magnitude was reached in transient transfection experiments performed in BHK cells.

Eukaryotic promoters are often controlled by multiple regulatory proteins, many of which are subjected to regulatory pathways involving other transcriptional regulators and/or to autoregulatory pathways. This has been noted in particular for promoters that drive the expression of developmentally-controlled genes that need to be expressed at high levels in given cells but totally shut-off in other nearby cells, specifically controlled by specific genetic switches. The functioning of such pathways is still incompletely understood. Nevertheless, as demonstrated by the present invention, one may mimic the principles and advantages of such natural networks with just two regulatory proteins functioning in a cross-regulatory network, and that such a regulatory network approach leads to more efficient silencing of basal expression in comparison with traditional systems.

Taken together, the major distinction of the regulatory system of the present invention compared to other vectors available in the art is that the target gene is either actively silenced or activated, depending on the absence or presence of the ligand (FIG. 1). In the absence of dox, TetR-KoxW actively silences the transgene which is, in addition, depleted of transcriptional activators as expression of the latter is simultaneously silenced by the repressor TetR-KoxW. This results in extremely low level expression in the "off-state." In the presence of dox, the "on-state," the repressor no longer inhibits the expression of the transgene and that of GAL4-VP16, which leads to a gradual increase in concentration of transactivator which, in turn, will activate the derepressed target gene. Eventually target gene expression is amplified by both, derepression and direct transcriptional activation.

As mentioned above, regulatory networks of the present invention were found to be capable of generating induction windows of over three orders of magnitude of transgene expression. See the right-most data set in FIG. 2. Traditional expression vectors known in the art mediated relatively high level of basal expression and relatively low induction windows (typically 10 to 50 fold induction) when tested in transient transfection experiments. This induction ratio may be improved in stable transfection experiments or in transgenic animals, where particular chromatin environment of the transgene may act to repress basal but not induced expression, thereby increasing the effectiveness of regulation. However, the selection of a proper chromosomal environment of the transgene often demands a careful selection of the cell line, or of the considered tissue in selected transgenic animal strains. See, for example, Yin et al., Anal Biochem. 235: 195–201 (1996). The selection will be difficult for most in vivo gene therapy vectors, as they do not allow selection of the transgene insertion site within the cell chromosomes. However, regulatory networks of the present invention may be more easily amenable to reliable use in vivo. For example, the built-in regulatory capacity of networks may make them less dependent upon other regulatory events, such as chromatin structure near the transgene insertion, to achieve efficient transgene control.

EXAMPLE 5
Comparison with Other Doxycycline-dependent Systems

The network of regulatory proteins of the present invention was compared to commercially-available (Clontech®) regulatory systems based on the fusion of the VP16 activation domain to TetR (the tTA-based Tet-Off system) and to the reverse TetR (the rtTA-dependent Tet-On system).

5.1 Plasmid construction

The pSV-TetRNLS-KoxW and pSV-TetRNLS-TR$_{450}$W constructs were prepared as described in Experiment 3.1.

The rtTA-dependent Tet-On construct and the tTA-based Tet-Off construct were prepared by pTet-On equivalent to puHD17-1 [Gossen et al., Science 268: 1766–1769 (1995)], pTet-Off equivalent to puHD15-1 neo [Resnitsky et al., Molec. Cell. Biol. 14: 1669–1679]; (1994); pTRE-Luc equivalent to pUHC13-3 [Gossen, & Bujard, Proc. Natl. Acad. Sci USA, 89, 5547–5551 (1992)].

5.2 Cell culture and transfection $C_2C_{12}$ cells were cultivated and transfected essentially as described in Example 3.2. The conditional expression vector pVG-GTTI-Luc+ was constructed by ligating a fragment containing seven TREs, five GAL4 sites, the TATA box and initiator sequence upstream of the coding region of GAL4VP16 to a fragment in which another TATA box and initiator sequence are located upstream of the luciferase coding region, such that the GAL4VP16 and luciferase genes are bidirectionally regulated.

$C_2C_{12}$ cells were co-transfected with 162 ng of pVG-GTTI-Luc+ (a fusion of the p5xGTTI-GAL4-VP16 expression vector and p5xGTTI-Luc+ reporter with bi directional transcriptional regulation), 162 ng of the pCMVβGal, and 810 ng of either pSV-TetRNLS-TR$_{450}$W, pSV-TetRNLS-KoxW, pUHG17-1 (Tet-On), or pTet-OFF. For transfections, cells were seeded in 24 well. plates at about 40% confluency and allowed to attach to the surface. After washing with PBS, cells were exposed to the transfection mix for 4 hours. Thereafter, the transfection mix was replaced by medium which contained, where indicated, 100 ng/ml dox hydrochloride (Sigma #D9891). Cells were incubated in presence or absence of 100 ng/ml of doxycycline in the culture medium for 48 hr, after which cell extracts were prepared for luciferase and β-galactosidase assays.

5.3 Extract preparation and enzymatic measurements

Extract preparation and enzymatic measurements were conducted essentially as described in Example 1.3.

Figure 4B:
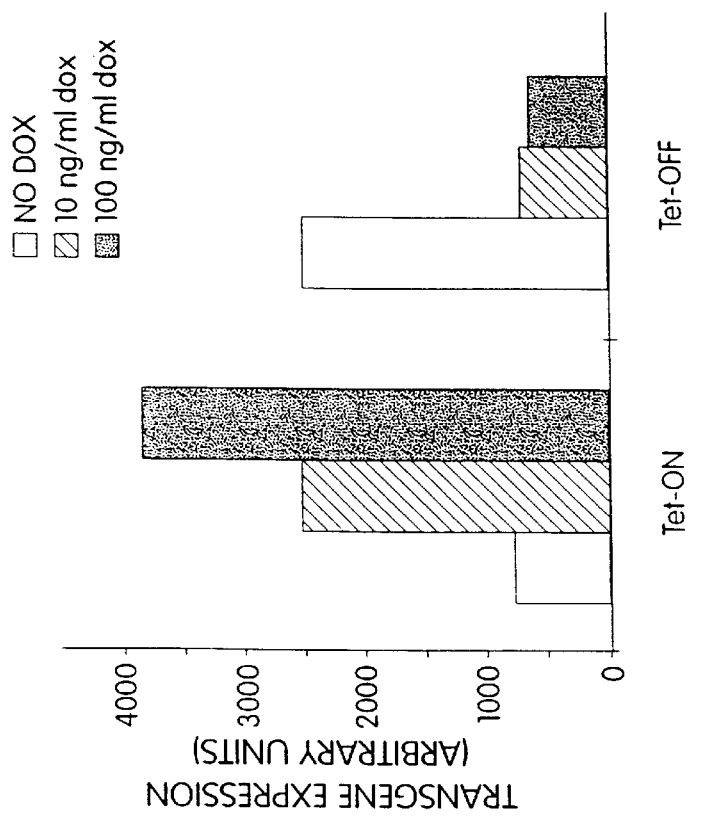
FIGS. 4A and 4B are bar graphs depicting the regulatory network in $C_2C_{12}$ cells (Panel A) and comparison with Tet-On and Tet-Off expression vectors (Panel B). $C_2C_{12}$ cells were co-transfected with pVG-GTTI-Luc+ (a fusion of the p5xGTTI-GAL4-VP16 expression vector and p5xGTTI-Luc+ reporter with bi-directional transcriptional regulation), the pCMVβGal, and either pSV-TetRNLS-TR$_{450}$W or pSV-TetRNLS-KoxW (Panel A) or pUHG17 (Tet-On), or pTet-OFF (Panel B). Cells were incubated in the absence of dox (open bars) or in the presence of 10 ng/ml (cross-hatched bars) or 100 ng/ml (solid bars) of dox. Transgene expression of luciferase was normalized to that of β-galactosidase and is expressed in relative light units.
Figure 4A:
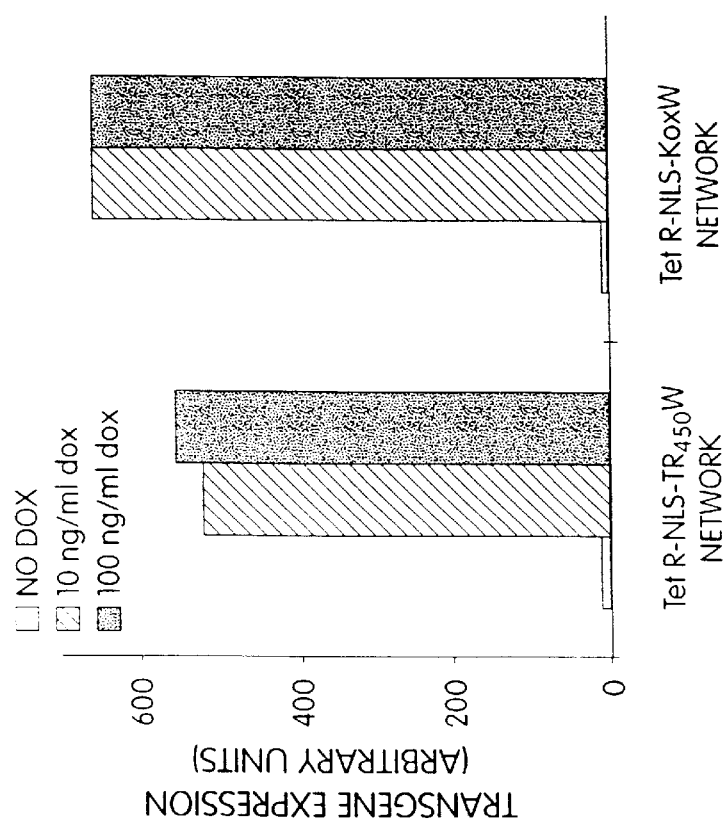

As expected, the tTA-based Tet-Off system resulted in a loss of activation in response to dox, while the rtTA-dependent Tet-On system yielded an increase in transgene expression in $C_2C_{12}$ cells (FIG. 4B). However, the network of regulators of the present invention was more efficient in terms of the window of induction, which was 10 to 100 fold wider with the network of regulatory proteins, and in terms of efficient silencing of the transgenes, yielding 20 to 100 fold lower uninduced activities. Similar differences were noted with BHK cells (data not shown). In addition, the regulatory network system appears to be more sensitive with respect to dox concentration as compared to transgene induction using the Tet-On vectors (compare FIGS. 4A and 4B).

EXAMPLE 6
Kinetics of Induction of the Network of Regulatory Proteins

To examine the kinetics of dox-induced gene expression mediated by the network of regulatory proteins of the present invention, the time course of induction of luciferase activity in $C_2C_{12}$ cells was monitored after addition of dox to the medium (final concentration 100 ng/ml). For comparison purposes, the kinetics of dox-induced gene expression was also determined for the tTA-based Tet-Off system and the rtTA-dependent Tet-On system. Cells were cultured and transfected essentially as described in Experiment 5.2, except that pPGK-TetRNLS-TR$_{450}$W was used to express the repressor. Briefly, cells were incubated for a total time of 72 hr until cell extracts were prepared for luciferase and β-galactosidase assays, either in the absence or presence of 100 ng/ml of dox in the culture medium for the indicated time. Luciferase and β-galactosidase assays were conducted essentially as described in Experiment 5.3. For direct comparison, all activities are normalized to those obtained in non inducing conditions, i.e., in the absence of dox for Tet-On and for GAL4-VP16/TetR-TR$_{450}$W or in the presence of dox for Tet-Off, which were given an arbitrary value of 1.

Figure 5:
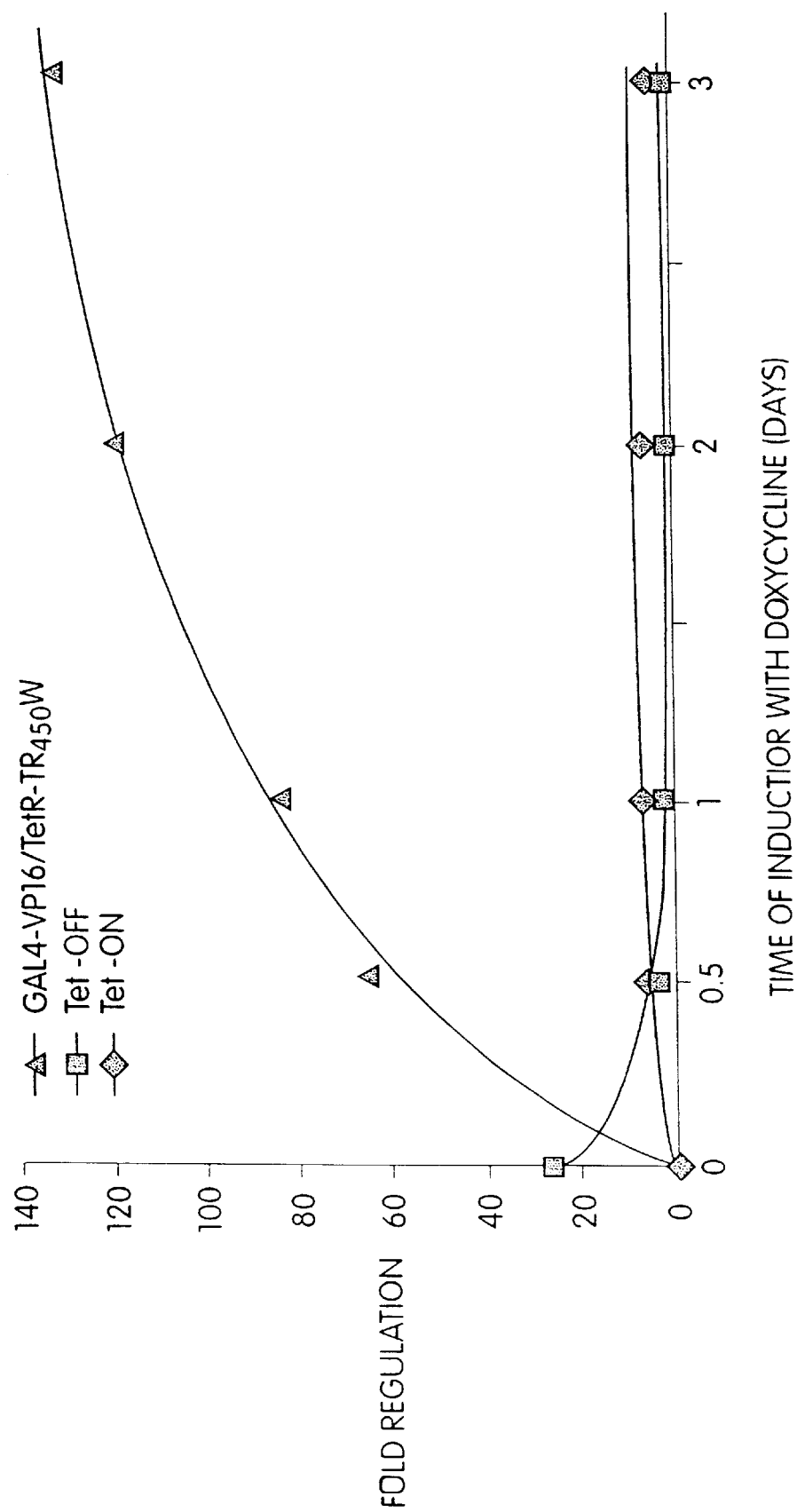
FIG. 5 is a line graph depicting the time course for the regulatory network in $C_2C_{12}$ cells and comparison with Tet-On and Tet-Off expression vectors. $C_2C_{12}$ cells were co-transfected with the pCMVβGal, and with either pVG-GTTI-Luc+ and pPGK-TetRNLS-TR$_{450}$W (solid triangles), or pUHG17 and Clontech®'s pTRE-Luc reporter (Tet-On, solid diamonds), or pTet-OFF and pTRE-Luc (Tet-Off, solid squares). Cells were incubated in the absence or presence of 100 ng/ml of dox. Activities of luciferase were normalized to those of β-galactosidase and are expressed as relative light units. For direct comparison, all activities are normalized to those obtained in non inducing conditions, i.e., in the absence of dox for Tet-On and for GAL4-VP16/TetR-TR$_{450}$W or in the presence of dox for Tet-Off, which were given an arbitrary value of 1.

When compared for the kinetics of induction in parallel experiments, the TR$_{450}$W based system showed a faster kinetic of induction as compared to the Tet-On and Tet-Off systems, despite a somewhat longer lag phase of the regulatory network (FIG. 5). For instance, after a 12 hours induction period, the TR$_{450}$W based vectors allowed a 60 fold activation of the transgene expression, while a 9 fold repression and 6 fold activation of the transgene were observed with Tet-Off and Tet-On, respectively. Similar differences were obtained when using the KoxW-based network system (data not shown).

Equivalents

From the foregoing detailed description of the specific embodiments of the invention, it should be apparent that a unique regulatory system for controlled transgene transcription has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of the particular inducer ligand, or the particular activator and repressor proteins is believed to be a matter of routine for a person of ordinary skill in the art with knowledge of the embodiments described herein.

What is claimed is:

1. A system for controlled transcription of a transgene comprising:

(a) a chimeric repressor protein comprising a DNA-binding tetracycline repressor fused to at least two distinct multimerized eukaryotic transcriptional repression domains;

(b) a tetracycline inducer which, when present, binds to the repressor protein; and (c) a transactivator which activates expression of said transgene and of its own gene in an autoregulatory positive feedback loop when the repressor protein is bound to the tetracycline inducer.

2. The system of claim 1 wherein the repressor protein comprises a fused multimer of at least two distinct repression domains selected from the group consisting of hMAD, mSin3A, HDAC1, eve, WRPW, hTLE1, rTR-HBD, cEcR, E4BP4, WT1, Kox and MeCP2.

* * * * *

SEQUENCE LISTING

<160> NUMBER OF SEQ ID NOS: 11

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: PCR Primer

<400> SEQUENCE: 1
cggaattcac catgtctaga ttagataaaa gtaaag                              36

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 2
cgggatccac tttcacattt aagttgtttt                                     30

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Insertion
      Oligor

<400> SEQUENCE: 3
gatctccaaa aagaagaga aagg                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Insertion
      Oligor

<400> SEQUENCE: 4
gatccctttc tcttcttttt tgga                                           24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Insertion
      Oligor

<400> SEQUENCE: 5
gatcctggag accatggtag c                                              21

<210> SEQ ID NO 6

```
<211> LENGTH: 21
<212> TYPE: DNA
<213> ORGANISM: Artificial Sequence
<220> FEATURE:
<223> OTHER INFORMATION: Description of Artificial Sequence: Insertion
      Oligor

<400> SEQUENCE: 6
ggccgctacc atggtctcca g                                              21

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 7
cgagatcttt gactgtatcg ccggaattc                                      29

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: PCR Primer

<400> SEQUENCE: 8
ggcggccgct aggatccagt ctctgaatca ggatgggt                            38

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 9
cgggatccgg catggcaaca gacctgg                                        27

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 10
ggcggccgct cagtcctcaa agacttccaa                                     30

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: PCR Primer

<400> SEQUENCE: 11
ggcggccgct accaaggtct ccatgggaag agaggcggga agag                     44
```